United States Patent [19]

Ross

[11] 3,979,445

[45] Sept. 7, 1976

[54] PROCESS FOR PRODUCING AMINO G ACID AND AMINO J ACID FROM TOBIAS ACID

[75] Inventor: Lawrence James Ross, Martinsville, N.J.

[73] Assignee: American Cyanamid Company, Stamford, Conn.

[22] Filed: Sept. 19, 1975

[21] Appl. No.: 615,135

[52] U.S. Cl. .................................................. 260/508
[51] Int. Cl.² .......................................... C07C 143/60
[58] Field of Search .................................... 260/508

[56] References Cited
UNITED STATES PATENTS 1,969,189  8/1934  Tinker et al. ...................... 260/508

Primary Examiner—James O. Thomas, Jr.
Assistant Examiner—Nicky Chan
Attorney, Agent, or Firm—John L. Sullivan

[57] ABSTRACT

A novel process for producing 2-amino-6,8-naphthalenedisulfonic acid (Amino G Acid) and 2-amino-5,7-naphthalenedisulfonic acid (Amino J Acid) which comprises heating 2-amino-1-naphthalenesulfonic acid (Tobias Acid) in 100% sulfuric acid, sulfonating the heated mixture with sulfur trioxide at a temperature in the range of 90°C. to 150°C. and hydrolyzing the sulfonation product.

5 Claims, No Drawings

PROCESS FOR PRODUCING AMINO G ACID AND AMINO J ACID FROM TOBIAS ACID

The present invention is directed to a new method for the production of 2-amino-6,8-naphthalenedisulfonic acid (Amino G Acid) and 2-amino-5,7-naphthalenesulfonic acid (Amino J Acid) from 2-amino-1-naphthalenesulfonic acid (Tobias Acid). The two aminonaphthalenedisulfonic acids are used as intermediates in the production of dyes.

When 2-naphthylamine (BNA) is sulfonated in oleum, the sulfonation products are principally 2-amino-1,5,7-naphthalene trisulfonic acid and 2-amino-6,8-naphthalenedisulfonic acid (Amino G Acid). Hydrolysis of the trisulfonic acid provides Amino J Acid (2-amino-5,7-naphthalenedisulfonic acid). Thus, using this so-called BNA route, it is possible to prepare a fixed ratio of both Amino J Acid and Amino G Acid. However, because of the known carcinogenicity of 2-naphthylamine, this route is not used. Amino J Acid is primarily made by the sulfonation of 2-amino-1-naphthalenesulfonic acid (Tobias Acid) with 30% oleum followed by hydrolysis of the intermediate 1,5,7-trisulfonic acid. Amino G Acid, on the other hand, is made by the sulfonation of beta naphthol with sulfuric acid and then with 20% oleum, in controlled steps from 15°–80°C., followed by amination by the Bucherer Reaction.

We have now discovered that addition of sulfur trioxide to Tobias Acid in hot 100% sulfuric acid provides both 2-amino-1,5,7-naphthalenetrisulfonic acid and Amino G Acid. Separation of Amino G Acid and hydrolysis of the trisulfonic acid provides Amino J Acid.

This represents a new method for the preparation of Amino G Acid along with Amino J Acid, both from Tobias Acid.

It was previously known that Tobias Acid rearranges in hot 100% sulfuric acid to the 6- and/or 8-sulfonic acid, but it was not known that the rearranged product could be further sulfonated by the addition of sulfur trioxide in hot 100% sulfuric acid to give the 6,8-disulfonic acid.

Depending on the conditions used in the reaction, the ratio of Amino J Acid to Amino G Acid can be varied to favor formation of one or the other. Conditions favoring rearrangement favor production of Amino G Acid, i.e., long periods of heating at elevated temperature prior to addition of the sulfur trioxide.

Generally speaking, the reaction mixture containing 2-amino-1-naphthalenesulfonic acid in 100% sulfuric acid is heated for a period of time from about 1 to several hours before addition of sulfur trioxide at a temperature of about 80°–150°C., preferably 100°–120°C. in order to rearrange the Tobias Acid to the 6- and/or 8-sulfonic acid. The sulfur trioxide either gaseous or liquid, preferably liquid, is added and the reaction continued at a temperature of about 90°–150°C., preferably 100°–120°C., for a period of at least about 2 hours and preferably about 5 to 10 hours. The reaction mixture is then diluted with water and heated to hydrolyze 2-amino-1,5,7-naphthalenetrisulfonic acid to 2-amino-5,7-naphthalenedisulfonic acid. The products are isolated by conventional methods, as described in the accompanying examples.

The rearrangement of 2-amino-1-naphthalene-sulfonic acid to form 2-amino-6-naphthalenesulfonic acid, 2-amino-8-naphthalenesulfonic acid or mixtures thereof is conducted under conditions of temperature and reaction time which will vary depending on the desired ratio of the 2-amino-6,8-naphthalenedisulfonic acid (Amino G Acid) and 2-amino-5,7-naphthalenedisulfonic acid (Amino J Acid) in the final product. For instance, when the rearrangement is conducted at a temperature above 80°C., preferably in the range of 100°C. to 120°C., for a period of over an hour, preferably 1.5 to 10 hours and most preferably 2 to 8 hours, the formation of Amino G Acid in the final product is favored, and consequently a higher ratio of Amino G Acid to Amino J Acid results. However, if the rearrangement is conducted below 80°C., the ratio of Amino G Acid of Amino J Acid in the final product is considerably lower. The reaction is conducted using a weight ratio of 2-amino-1-naphthalenesulfonic acid (or its alkali metal salts) to sulfuric acid in the range of about 1:1 to 1:10, preferably 1:2 to 1:6.

The sulfonation reaction between the rearranged product mixture and sulfur trioxide is carried out at a temperature in the range of 90°C. to 150°C., preferably 100°C. to 120°C., for a period of at least an hour and up to 5 to 6 hours. A suitable mole ratio of 2-amino-1-naphthalenesulfonic acid to sulfur trioxide for the reaction is in the range of about 1:1 to 1:20, preferably 1:2 to 1:1.

The hydrolysis of the sulfonation reaction product can be conducted by refluxing the sulfonation reaction product after dilution with water. Alternatively, the diluted sulfonation reaction product can be heated to a temperature in the range of 90°C. to 130°C., preferably 110°C. to 120°C. The amount of water used to dilute the sulfonation reaction product is not critical as long as the hydrolysis takes place on heating. However, for optimum results, it is preferred that a weight ratio of sulfonation reaction product to water, or dilute solutions of electrolytes, such as sodium chloride, of at least 1:1, and preferably from 1:1.2 to 1:10 be used.

The invention is illustrated by the following examples.

EXAMPLE 1

A reaction vessel was charged with 51.4 grams (28 ml.) of concentrated sulfuric acid and 30.4 grams (16 ml.) of 30 percent oleum to form 81.8 grams of 100 percent sulfuric acid. To this was added 44.6 grams (0.2 moles) of 2-amino-1-naphthalenesulfonic acid. The mixture was heated to 110°–115°C. and 32.5 grams (19 ml., 0.44 mole) of liquid sulfur trioxide added dropwise over a period of 45 minutes. The reaction mixture was then heated at 110°–115°C. for 6 hours, cooled to room temperature and diluted with 10 ml. water. The diluted mixture was then heated at 110°C. for 3 hours, diluted with 135 ml. of water and cooled to 15°C. A yellow solid was formed which was separated by filtration. The separated solid was dissolved in 200 ml. of water. Thereafter, 40 grams of sodium chloride was added and the precipitate produced (47.8 grams) was separated and dried.

The dried precipitate was found to contain 24.36 grams (0.08 mole) of 2-amino-6,8-naphthalenedisulfonic acid and 11.39 grams (0.38 mole) of 2-amino-5,7-naphthalenedisulfonic acid. The mother liquors afforded an additional 6.97 grams (0.023 mole) of 2-amino-6,8-naphthalenedisulfonic acid and 7.73 grams (0.025 mole) of 2-amino-5,7-naphthalenedisulfonic acid.

The overall yield of 2-amino-6,8-naphthalenedisulfonic acid was 51.5 percent. The overall yield of 2-amino-5,7-naphthalenedisulfonic acid was 31.5 percent.

EXAMPLE 2

This example illustrates that by lowering the reaction temperature of the rearrangement of 2-amino-1-naphthalenesulfonic acid, the yield of 2-amino-6,8-naphthalenedisulfonic acid in the final product decreases substantially while the yield of 2-amino-5,7-naphthalenedisulfonic acid is increased.

A reaction vessel was charged with 62.8 grams (34 ml.) of concentrated sulfuric acid and 37.2 grams (19.3 ml.) of 30 percent oleum to form 100 grams of 100 percent sulfuric acid. To this 44.6 grams (0.2 mole) of 2-amino-1-naphthalenesulfonic acid was added to form a mixture. After heating the mixture to 60°C., 32.0 grams (0.4 mole) of liquid sulfur trioxide was added dropwise over a period of 35 minutes with the temperature being gradually raised to 100°C. The reaction mixture was held at 100°C. for 6 hours and cooled to room temperature. The cooled reaction mixture was diluted with 170 ml. of water and further cooled to 20°C. Thereafter, the mixture was refluxed for 3 hours and the precipitate which formed was separated by filtration.

The overall yield of 2-amino-6,8-naphthalenedisulfonic acid was 9.5 percent. The overall yield of 2-amino-5,7-naphthalenedisulfonic acid was 46 percent.

I claim:

1. A process for the preparation of 2-amino-6,8-naphthalenedisulfonic acid and 2-amino-5,7-naphthalenedisulfonic acid comprising the steps of: (1) heating a solution of 2-amino-1-naphthalenesulfonic acid in 100% sulfuric acid at a temperature of from about 80°C. to about 150°C. to effect rearrangement of the 2-amino-1-naphthalene sulfonic acid to the corresponding 6- or 8-naphthalenesulfonic acid, (2) sulfonating the reaction product from step 1 with sulfur trioxide at a temperature of from about 90°C. to about 150°C. to produce a reaction product comprising 2-amino-6,8-naphthalenedisulfonic acid and 2-amino-1,5,7-naphthalenetrisulfonic acid and (3) hydrolyzing the reaction product of step 2 to convert the 2-amino-1,5,7-naphthalenetrisulfonic acid to 2-amino-5,7-naphthalenedisulfonic acid.

2. The process according to claim 1 wherein the hydrolysis is conducted in the presence of water at a temperature of from 90°C. to 130°C.

3. The process according to claim 1 wherein the weight ratio of 2-amino-1-naphthalenesulfonic acid to sulfuric acid is from 1:1 to 1:10 and the mole ratio of 2-amino-1-naphthalenesulfonic acid to sulfur trioxide is from 1:1 to 1:20.

4. The process according to claim 1 wherein the weight ratio of the 2-amino-1-naphthalenesulfonic acid to the sulfuric acid is in the range of 1:2 to 1:6 and the mole ratio of the 2-amino-1-naphthalenesulfonic acid to the sulfur trioxide is in the range of 1:2 to 1:1.

5. The process according to claim 1 wherein the rearrangement reaction is conducted at a temperature in the range of 100°C. to 120°C. and the sulfonation reaction is conducted at a temperature in the range of 100°C. to 120°C.

* * * * *